United States Patent
Lovoi (10) Patent No.: US 8,114,005 B2
(45) Date of Patent: Feb. 14, 2012

(54) METHOD FOR MODIFYING SKIN DISTANCE FROM A BRACHYTHERAPY BALLOON APPLICATOR

(75) Inventor: Paul A. Lovoi, Saratoga, CA (US)

(73) Assignee: Xoft, Inc., Freemont, CA (US)

( * ) Notice: Subject to any disclaimer, the term of this patent is extended or adjusted under 35 U.S.C. 154(b) by 1146 days.

(21) Appl. No.: 11/810,415

(22) Filed: Jun. 4, 2007

(65) Prior Publication Data

US 2008/0300443 A1    Dec. 4, 2008

(51) Int. Cl.
*A61N 5/00* (2006.01)
(52) U.S. Cl. .......................................................... 600/1
(58) Field of Classification Search ................. 600/1–8; 604/93.01, 96.01, 97.01, 590.1, 591.1
See application file for complete search history.

(56) References Cited

U.S. PATENT DOCUMENTS

| | | | |
|---|---|---|---|
| 5,387,450 A | 2/1995 | Stewart | |
| 6,923,754 B2 * | 8/2005 | Lubock | 600/3 |
| 7,563,223 B2 * | 7/2009 | Sampson | 600/3 |
| 2006/0259027 A1 * | 11/2006 | Kwan et al. | 606/41 |
| 2007/0191668 A1 * | 8/2007 | Lubock et al. | 600/3 |

\* cited by examiner

*Primary Examiner* — Charles A Marmor, II
*Assistant Examiner* — Christine Hopkins
(74) *Attorney, Agent, or Firm* — Thomas M. Freiburger; William A. Loginov; Loginov & Associates, PLLC (57) ABSTRACT

In brachytherapy radiation treatment, particularly on the breast following a tumor resection, adequate skin to balloon distance must be maintained, to avoid damage to the skin. Often the distance is too small in certain areas or at a single point. The disclosed procedures and devices are effective to manipulate the skin-to-balloon distance to increase that distance when necessary, using vacuum, friction or other means to grip, move and "bunch" the breast tissue from regions of larger balloon-skin distance to regions with inadequate balloon-skin distance. The apparatus can include a ring or ring shaped array that fits around the breast, larger than the balloon, a circular vacuum device, or a cup which is pushed over the breast to move tissue toward a thin tissue region. In many cases only a few millimeters of added distance are needed to meet minimum requirements so that the radiation procedure can commence.

18 Claims, 7 Drawing Sheets

METHOD FOR MODIFYING SKIN DISTANCE FROM A BRACHYTHERAPY BALLOON APPLICATOR

BACKGROUND OF THE INVENTION

This invention concerns radiation therapy, especially brachytherapy, for treating tissues which may have diffuse proliferative disease.

In brachytherapy, the radiation source is generally placed within a surgically created or naturally occurring cavity in the body. In particular, this invention relates to delivery of radiation therapy to glandular and adipose tissue as might be found in the human breast, or to other similar tissue which can be easily manipulated, often following surgical treatment of cancer.

Radiation therapy following tumor resection or partial resection is generally administered over a period of time in partial doses, or fractions, the sum of which comprises a total prescribed dose. This fractional application takes advantage of cell recovery differences between normal and cancerous tissue whereby normal tissue tends to recover between fractions, while cancerous tissue tends not to recover.

In brachytherapy, a prescribed dose is selected by the therapist to be administered to a volume of tissue (the target tissue) lying outside the treatment cavity into which the radiation source will be placed. Generally the prescribed dose will include a minimum dose to be delivered at a preferred depth outside the treatment cavity (the prescription depth). Since, in accordance with the laws of physics, radiation intensity falls off sharply with increasing distance from the radiation source, it is desirable to create and maintain a space between the source of radiation and the first tissue surface to be treated (generally the cavity wall since the source is placed within the cavity) in order to moderate the absorbed dose at the cavity surface. This is often done by placing a balloon or other applicator in the cavity with the radiation source inside the applicator.

Although not always the case, generally the absorbed dose at the prescription depth outside the cavity is to be uniform. In this isotropic case, it is therefore important that the incident radiation on the interior surface of the cavity be the same at all points being treated. To accomplish this objective, it may be necessary to sequentially position a single radiation source through a series of positions (or utilize multiple sources strategically placed) which, in the aggregate, produce a uniform absorbed dose incident on the cavity surface being treated. When this is achieved, the absorbed dose reaching into tissue will be the same at all points being treated, and the minimum prescribed dose can be delivered at the prescription depth as nearly as the treatment plan will allow. Furthermore, by selecting the radiation source intensity (radioisotope emissions or x-ray tube output) and controlling treatment time and the distance from the source(s) to the cavity interior surface, the incident radiation can be sufficiently moderated to avoid substantial damage to normal tissue.

In many instances, the treatment cavity may be near the skin such that the treatment plan, if isotropic, may include points at the prescription depth which lie outside the skin surface. If prescription depth at those points lies far enough outside the skin, too high a dose could be received at the skin, and the therapist may be forced to locally shield emitted radiation from within the treatment cavity (see copending application Ser. No. 11/471,277 incorporated by reference herein in its entirety), or to resort to anisotropic radiation sources. Such capabilities may not be readily available or practical. In such cases, and there are many, the patient may therefore be denied the advantages of brachytherapy.

One currently accepted standard in radiation therapy is that, for a one centimeter prescription depth of tissue, and for the applicator diameter range of intent, assuming the tissue at the prescription depth receives the desired dose (1×), the tissue nearest the source should not receive more than 2.5× to 3× the prescription dose. Standards also usually require that the skin not receive a dose of more than 1.5× the prescription dose. With a one centimeter prescription depth, this usually requires the skin be at least 6-8 mm out from the surface of a balloon applicator engaged against the tissue in a cavity. A distance of less than about 6-8 mm may result in doses higher than 1.5× the prescription dose which are known to often result in undesirable cosmesis. This problem commonly arises in breast brachytherapy and is a counter-indication for brachytherapy. In order to make brachytherapy available to more patients having resection cavities in close proximity to skin surfaces or to other radiation sensitive structures, the apparatus and/or methods of this invention may be employed.

SUMMARY OF THE INVENTION

This invention employs external temporary fastenings to skin which are then manipulated in order to bunch the tissue volume overlying the treatment cavity into a smaller area. Because the tissue underlying the skin tends to follow lateral skin displacement, this effectively thickens the tissue layer and thus the separation between the cavity and skin surface. A simple example of such a device and method is a purse-string suture, the application of which, on tightening, draws the purse-string diameter inward. In this manner, a 5 mm separation can be transformed into a 7 mm separation, thus making isotropic brachytherapy an acceptable mode of radiation therapy. One embodiment of this invention comprises an array of individual vacuum tubes or cups, for example, which can be drawn into closer proximity after attaching their distal ends to the skin by applying vacuum, and then by compacting their arrangement. Such an array of tubes might be joined to a common manifold to facilitate concurrent vacuum application. Alternatively, each tube or cup can have its own vacuum source or be individually valved to permit sequential application of vacuum, and therefore attachment to the patient's skin.

Once joined to the skin with each tube or cup in proper starting position (before compaction), the tubes or cups can be compacted or drawn together, for example by tightening a belt, or alternatively where the tubes are splayed distally, by sliding a ring in the distal direction such that the tube distal ends and the skin to which they are secured are drawn together. The ring itself can be one whose diameter can be drawn smaller, with the suction ends or cups extending through the ring. A common tie-wrap would comprise a typical such ring.

A specific preferred embodiment comprises a hollow, sealed resilient structure. The distal surface of the structure is undulating in a manner to form concentric rings which when pressed into contact with the skin surface and evacuated, create a series of concentric vacuum chambers. The proximal crest of the undulations in the distal surface of each distal chamber has vents leading into the hollow interior of the structure such that all chambers are evacuated when vacuum is applied to the interior of the structure, and the device is thereby secured to the skin by the vacuum. The proximal surface of the structure has (at least partially) a series of radially-arranged undulations or ridges which abut the concentric chambers such that when vacuum is applied to the interior of the structure through a valved port leading to a vacuum source, the concentric undulations abut the ridges or radial undulations such that the structure cannot collapse and block the vacuum connection between the interior of the structure and the concentric chambers. The totality of the structure has sufficient resilience that it adjusts (or can be adjusted) into vacuum-tight contact with the skin contour of interest, whether concave, convex or of another complex configuration.

When positioned on the skin overlying the treatment cavity, evacuating the interior of the structure will additionally tend to draw the structure to a smaller overall diameter, thus forcing the concentric chambers closer together and concentrating the tissue over the cavity, bunching the skin and underlying tissue. This reduction in the diameter of the applicator device can be manually urged toward a desired configuration, or a drawstring or belt can be applied to the outside diameter of the applicator to effect such change.

In order to enhance a vacuum-tight seal with the skin, the distal outer surface of the device may be coated with a medical grade adhesive (for example, an adhesive as disclosed in U.S. Pat. No. 5,387,450) or an adherent hydrogel or similar material to seal small vacuum leaks or sealing imperfections between the device and the skin. Alternatively, the skin can be wetted with a semi-adherent gel or viscous coating.

In another embodiment of the device described, the device can be secured to a more rigid proximal element shaped so as to produce a desired contour in the skin contacting surface. After securing the resilient, distal portion of the device to the skin, a secondary vacuum chamber formed under the proximal element is actuated, for example by application of vacuum independently of the skin fastenings, to draw the resilient member and skin toward the desired contour. An example of this embodiment of the invention is a cup shaped vacuum device, with a generally annular vacuum chamber formed against the skin at its rim, and with more extreme curvature internally than the natural contour of the breast. The cup is engaged around a critical region where balloon-to-skin distance is inadequate. The edge of the cup first seals against the breast tissue at the cup rim, and when a vacuum is drawn on the interior of the device independently of the rim device, the breast is forced toward conformance with the device, making the distance from the skin to the balloon applicator larger in the critical region. In such an example, the vacuum may be applied independently of the internal volume of the cup as described above, or it may be applied concurrently. If concurrent, a dual vacuum chamber device may well be unnecessary.

In a simpler form of cup-shaped device only one vacuum chamber is involved, which is the interior of the cup. The applied vacuum seals the rim of the cup against the skin, and then draws the skin radially inwardly to bunch the tissue at a critical region.

Although the "footprints" of these embodiments are described as more or less circular, one of ordinary skill would be competent to adapt the principles disclosed to other shapes and therapeutic situations. The pattern of engagement of the skin (e.g., the breast) need not be a circuit but can contraction or bunching a force exerted from one direction, or from several directions, but not necessarily from all around the region of inadequate tissue depth. Also, engaging the device to cause the attendant tissue bunching, care must be taken to assure new cases of less-than-minimum tissue thickness have not been created. This can be assured by reimaging or by other remeasurement of the tissue.

The invention is not limited to use of vacuum cups or channels applied against the skin. For example, adhesive pads could be used, without the need for any vacuum chambers, such that an array of contact points are adhered to the skin, then the skin is manipulated to move and "bunch" tissue to increase the depth of tissue between the skin and the underlying cavity at a particular region. Such movement can be effected by a drawstring or belt, or by any appropriate form of mechanical device to move the temporary fastening points or adhesive contact points into a different pattern or configuration as desired. Generally, the movement is toward a smaller footprint of the array of contact points in order to accomplish the objective.

The invention generally encompasses manipulation of tissue by manipulation of the skin overlying or adjacent to the tissue. In particular, the invention is directed to tissue manipulation during brachytherapy in a human breast from which a lesion has been resected, resulting in an underlying cavity. The form of manipulation must be reliable and consistent and able to manipulate the tissue depth over a critical region in a reliable manner, without causing cavitation (separation) between the balloon of an applicator and the breast tissue at the surface of the resection cavity. The device is preferably removed from the skin between radiotherapy fractions.

It is therefore among the objects of the invention to facilitate brachytherapy treatment from within a resection cavity in situations where such treatment, at least conventional forms of such treatment, might be ruled out or limited due to inadequate distance from some areas of the patient's skin to the radiation source. This is accomplished by movement of tissue, and is particularly pertinent to breast brachytherapy, at and beneath the skin to "bunch" or thicken the depth of tissue in critical regions so that adequate distance is created and maintained between the radiation source and the skin at all points around the resection cavity. These and other objects, advantages and features of the invention will be apparent from the following description of a preferred embodiment, considered along with the accompanying drawings.

DESCRIPTION OF PREFERRED EMBODIMENTS

Figures 1A, 1B, 1C:
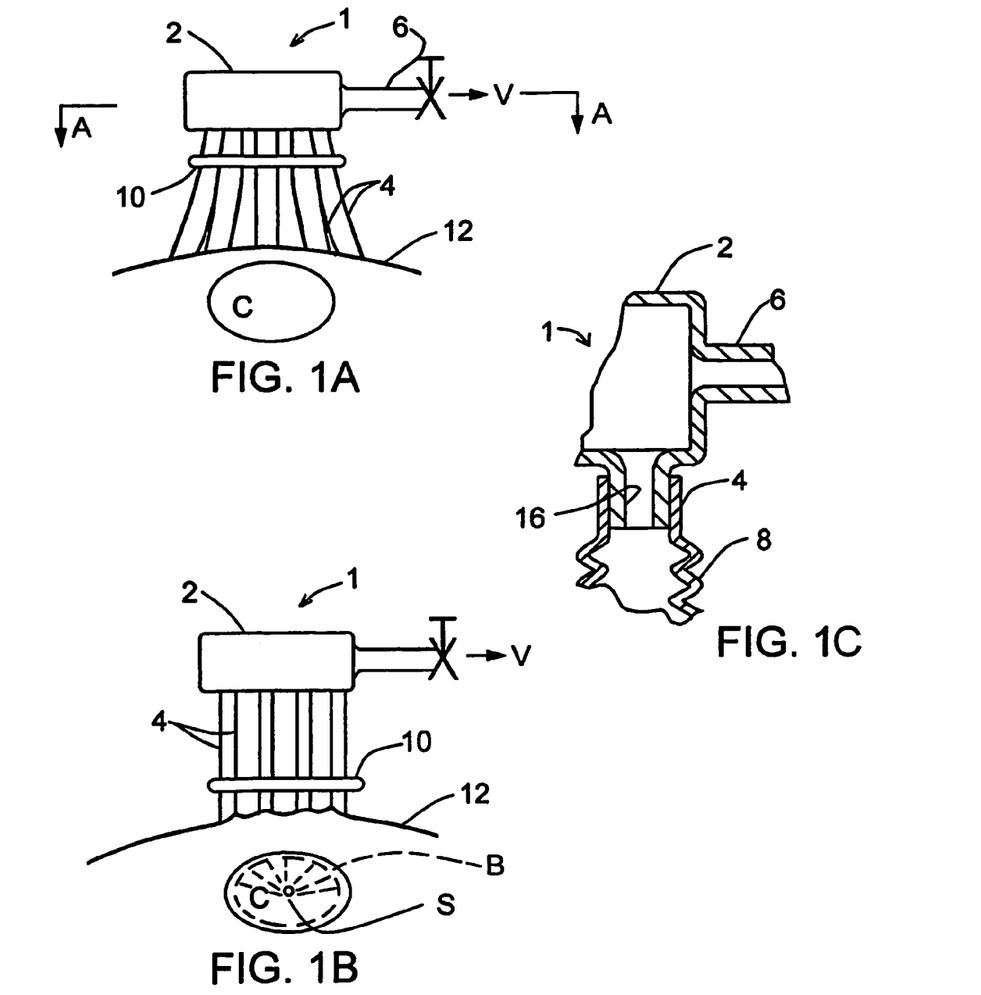
FIG. 1A is a side view of a multi-tube device of the invention with a vacuum manifold and a compacting ring shown positioned over a near-skin treatment cavity.
FIG. 1B shows the device of FIG. 1A applied to skin over a treatment cavity with the compacting ring advanced and the tubes compacted. The tissue is bunched and thickened over the treatment cavity
FIG. 1C shows manifold, vacuum port and tube detail of the device of FIGS. 1A and B in section.

An device embodiment 1 shown in FIG. 1A is positioned above a near-skin treatment cavity C of a patient. The device 1 comprises a central manifold 2 positioned proximally with respect to a series of tubes 4 separated or splayed apart from one another at their distal ends for suction contact with the skin 12 of the patient. The ends are positioned so as to be able to be compacted more closely together subsequently, bunching the skin to which they are attached. The array of ends of the tubes 4 define a diameter (or other, non-circular shape) larger than the underlying treatment cavity C resulting from the tumor resection. The manifold 2 has a port 6 which is valved and leads to a source of vacuum such as a pump or wall suction as might be present in a medical facility treatment room (neither pump nor wall suction is shown). The manifold is preferably of a relatively rigid material such as an engineering plastic like polycarbonate or polyethylene terephthalate (PET). The tubes 4 are preferably more resilient than the manifold 2 so as to be more easily positioned against the skin, and some or all may be at least partially formed in convolutions 8 as in shown in FIG. 1C to provide axial compliance to accommodate non-planar skin contours. If desired, the vacuum on the tubes may be individually controlled by conventional valving (not shown) rather than collectively through a manifold. Suitable tube materials include ionomer or silicone rubber. Positioned around and in contact with the array of the tubes 4 is a compacting ring 10. The ring 10 may be of a structural plastic (e.g., polycarbonate or Nylon), metal (e.g., stainless steel), or elastomer, (e.g., silicone rubber) which may be advanced distally after vacuum is applied in order to compact the tubes 4. FIG. 1B shows the compacting ring 10 having been advanced and bunching of the skin 12 and tissue overlying the treatment cavity C with an attendant increase in the skin-to-cavity tissue thickness.

FIG. 1C shows a partial section of the device 1 of FIGS. 1A and 1B, including a part of the manifold 2 near the vacuum port 6, and a method of joining the tubes 4 to the manifold 2. The method includes the manifold 2 having protruding nipples 16 to accommodate joining to the tubes 4. In FIG. 1C, an exemplary tube 4 is shown with the optional convolutions 8 mentioned above. With the proximal ends of the tubes sized to slip over the nipples 16, conventional bonding can be used to assemble the tubes to the manifold. Other conventional techniques known to those of skill in the art may also be used. FIG. 1B indicates a radiation source S in the treatment cavity C. In FIG. 1B the skin 12 is "bunched" together by the device 1 to increase the tissue depth between the skin and the cavity C, and from the skin to an applicator balloon B shown in dashed lines.

Figure 2:
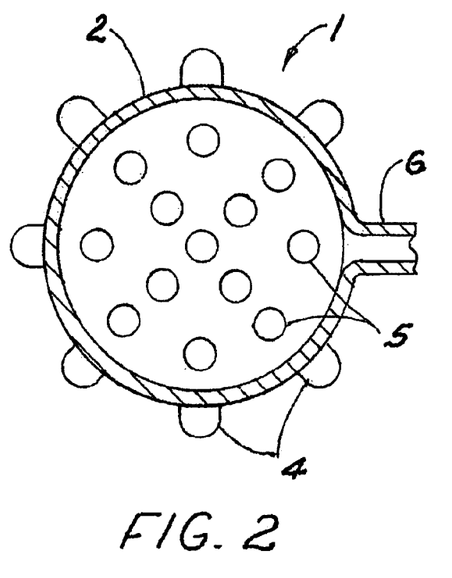
FIG. 2 is a section view in plan of the device from the line 2-2 as shown in FIG. 1A.

FIG. 2 shows the device 1 of FIG. 1a in section view as seen at 2-2, through the manifold 2. The array of tubes 4 are shown in a circular configuration and splayed, and the interior 5 of the nipples 16 are shown. Other tube layout configurations are optional with only minor design adjustments obvious to those of skill in the art.

Figure 3A:
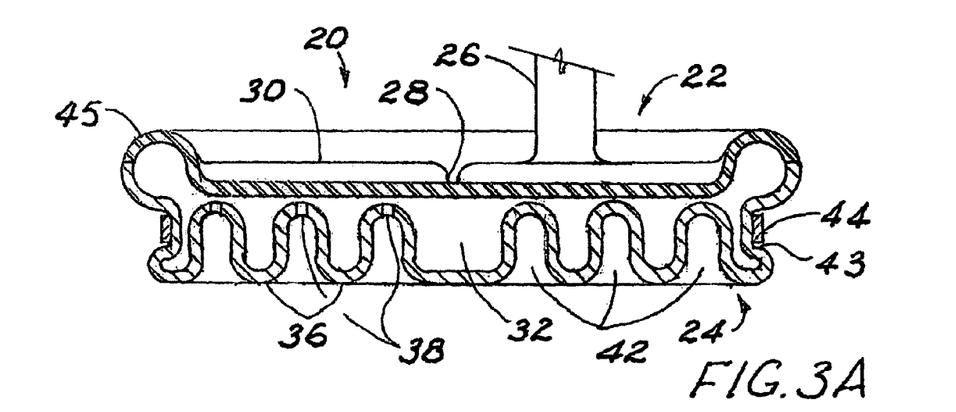
FIG. 3A is a side view of a preferred device in section showing radial and concentric undulations, and an outer, compacting belt.
Figure 3B:
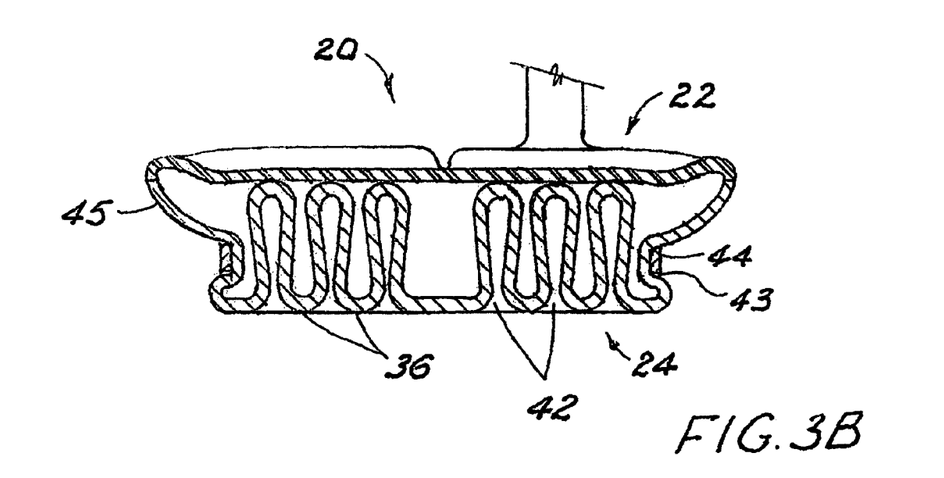
FIG. 3B is a side view of a preferred device in section showing the device of FIG. 3A after compaction of the concentric undulations and tightening of the belt.
Figure 3C:
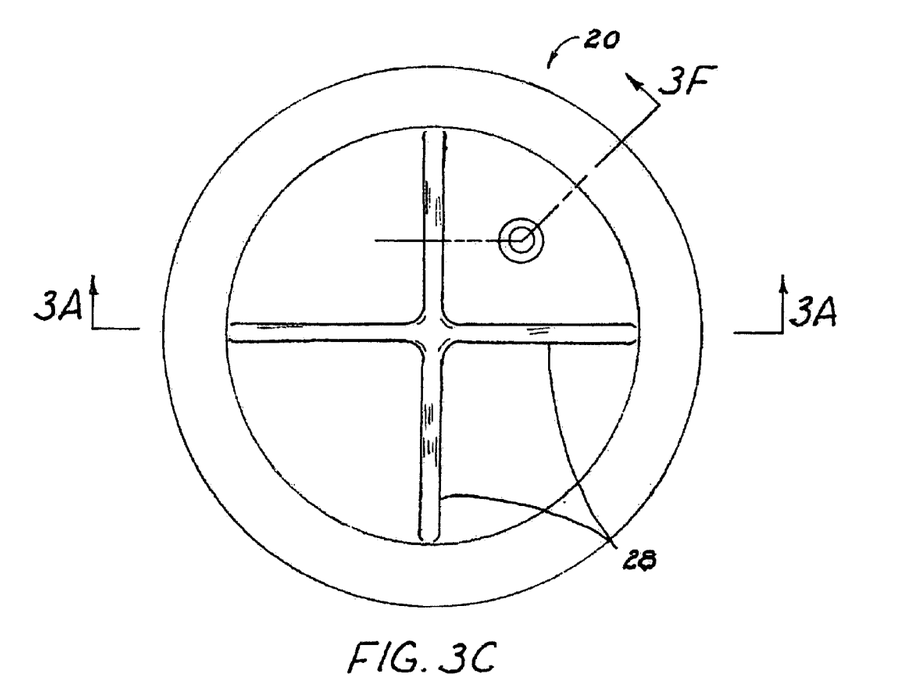
FIG. 3C is a top plan view showing radial undulations in the proximal surface of the device of FIG. 3A.

FIG. 3A shows a preferred embodiment of the invention in section view taken along the line 3A-3A in FIG. 3C. The device 20 has an upper (proximal) portion 22 and a lower (distal) portion 24. The proximal portion 22 has a valved vacuum port 26 leading to a vacuum pump or wall suction (valve not shown). The proximal portion 22 has radially extending undulations 28, functioning as downward ridges, as shown in FIGS. 3A and 3C. FIG. 3F shows one of the undulations in section. The undulations extend downwardly in the proximal outer wall 30 of the device 20, extending only along the lines 28 down into a manifold vacuum chamber 32. FIG. 3E shows simple ridges 29 for this purpose. The distal portion 24 of the device 20 has concentric undulations or corrugations 36 extending from the distal outer (or lower) surface of the device 20 and rising substantially into the manifold vacuum chamber 32 as shown, toward the radial undulations 28. The proximal and distal undulations nearly abut, but are not joined together. The radial undulations can comprise any form of spacer strips on the inner side of the upper wall 22. They can be in the form of molded solid ridges, or they can formed convolutions in the material of the upper portion 22 as shown. When vacuum is applied, the concentric undulations 36 bear against the radial ridges or undulations 28, holding the manifold vacuum chamber 32 open, as shown in FIG. 3B. At the proximal or inner crest of the concentric undulations 36 are ports 38 (the cutting plane for the sectional view of the ports is rotated 45° from the position shown in FIG. 3A) which communicate with the manifold vacuum chamber 32 of the device. These ports facilitate application of vacuum between the skin 5 of the patient and concentric vacuum chambers 42 formed by the concentric undulations 36.

FIG. 3B shows the device 20 of FIG. 3A, but after application of vacuum and attachment to the skin 12 (not shown). As may be seen, the diameter of the device 20 in contact with the skin is substantially reduced. If spontaneous reduction in diameter of device 20 fails to occur upon application of vacuum, and if manual assistance is inadequate or only temporarily creates the desired diameter reduction, a groove 43 and a belt 44 or any form of drawstring may be provided as shown in FIG. 3A at the outer periphery of the device 20 to assist in compacting the concentric undulations 36 of the rubbery distal portion, bunching the tissue overlying the treatment cavity C. Loops (as on pants for a belt, not shown) or other features may be needed to help locate the belt around the device periphery and to facilitate such compacting manipulation. As shown in FIG. 3A, a structure or configuration may be needed in the proximal portion 22 of the device to allow the distal portion 24 to easily reduce in diameter and bunch the tissue to which it is attached. In FIGS. 3A and 3B, such a structure is an outer toroidal ring 45 which deforms from a circular cross section in FIG. 3A to a more elliptical cross section in FIG. 3B, providing substantial independent radial mobility to the distal portion 24.

Although the concentric undulations 36 form separate concentric vacuum chambers 42 in the device as described above, other configurations can also be used. Furthermore, rather than collectively evacuated, concentric vacuum chambers 42 may be sequentially evacuated by providing conventional valving as known to those skilled in the art. As an example of an alternate configuration, a hexagonal matrix of separate cup-like chambers may be arrayed on the distal applicator surface, each cup in communication with a common or individual vacuum source, and each joined to its neighbors by a thin membrane to retain the vacuum, the membrane being adapted to crumple as the matrix is compacted after application to the skin by vacuum. Other configurations are also possible.

FIG. 3C shows a plan view from the proximal (or upper) side of the applicator 20 as seen in FIG. 3A, and shows the arrangement of the radial undulations 28. As mentioned above, other arrangements, e.g. simple radial ridges on the inner (lower) side of the wall 30, as shown in the partial section of FIG. 3E, are possible so long as they serve to hold the manifold vacuum chamber 32 (not shown in FIG. 3C) open when the manifold is evacuated.

Figure 3D:
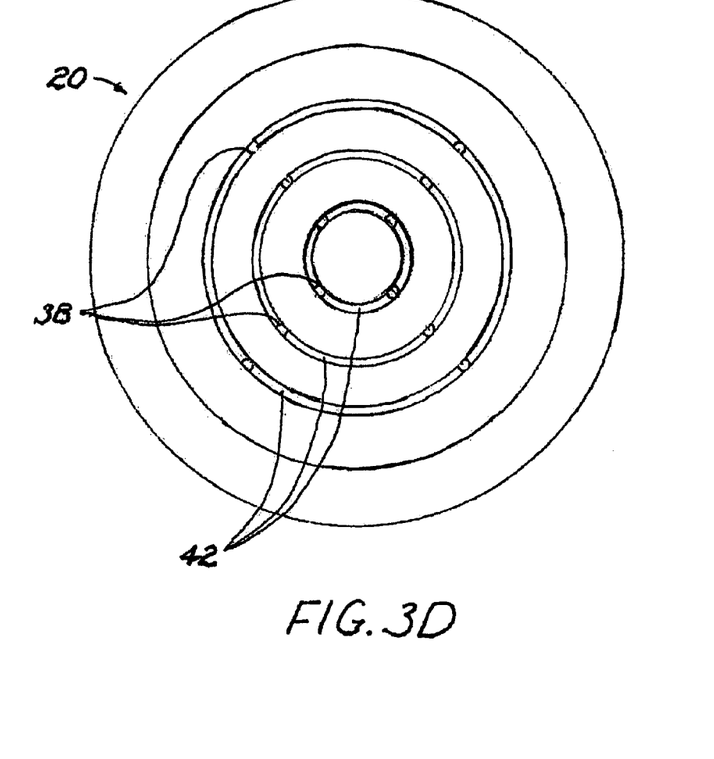
FIG. 3D is a bottom plan view of the device shown in FIG. 3B, showing the compacted concentric undulations in the distal surface and showing vacuum ports.
Figure 3E:
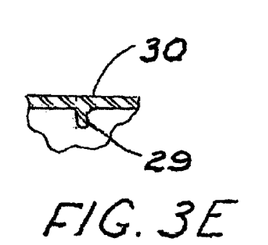
FIG. 3E is a partial sectional elevation view showing a ridge formed in the proximal wall of the device.
Figure 3F:
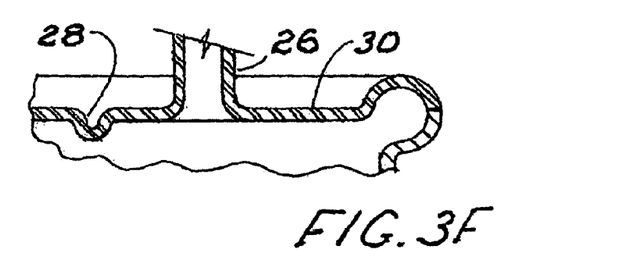
FIG. 3F is a partial sectional elevation, as seen along the line 3F in FIG. 3C, showing an undulation in the proximal wall of the device, an alternative to FIG. 3E.

FIG. 3D is a plan view of the device 20 of FIG. 3B from the distal side (sometimes referred to as the bottom side). The concentric vacuum chambers 42 and the vacuum ports 38 (shown in proper rotation in contrast to what is shown in FIG. 3A) are shown, communicating between the manifold vacuum chamber 32 and the concentric vacuum chambers 42.

In this embodiment the proximal portion 22 and the distal portion 24 may be one monolithic structure formed by roto-molding or blowmolding, or alternatively they may be pressure formed or molded in separate halves and joined by conventional techniques such as bonding or welding as is known to those of skill in the art. Suitable materials include silicone rubber, ionomer, ethylene propylene rubber, or similar materials. The distal portion 24 can be, as illustrated, an elastomeric structure, with the proximal wall 30 being metal or hard plastic, with appropriate bonding or sealing. The elastomeric portion includes at least the distal portion of the outer toroidal ring 45, and can include that entire toroidal ring.

This preferred embodiment is described as though the skin-contacting distal surface is planar before and after attachment to the skin for convenience in describing the device. The embodiment in fact need not be planar. The device can be fashioned so as to produce a skin-contacting surface (formed by the concentric undulations 36) which is contoured before and/or after attachment to the skin. One convenient method is to control the spacing between the abutting concentric and radial undulations within the vacuum chamber 32. For example, if the space between abutting undulations is minimal at the periphery of the device, and spaced apart toward the center as would result if the more-rigid proximal portion 22 is cupped, the distal portion 24 and skin contacting surface of the device will mimic the cupped shape of the proximal portion 22 when vacuum is applied. Furthermore, if sequential application of vacuum is used, outer concentric chamber 42 first, next compacting, and finally applying vacuum to inner chambers 42, an enhanced bunching will result.

Figure 4:
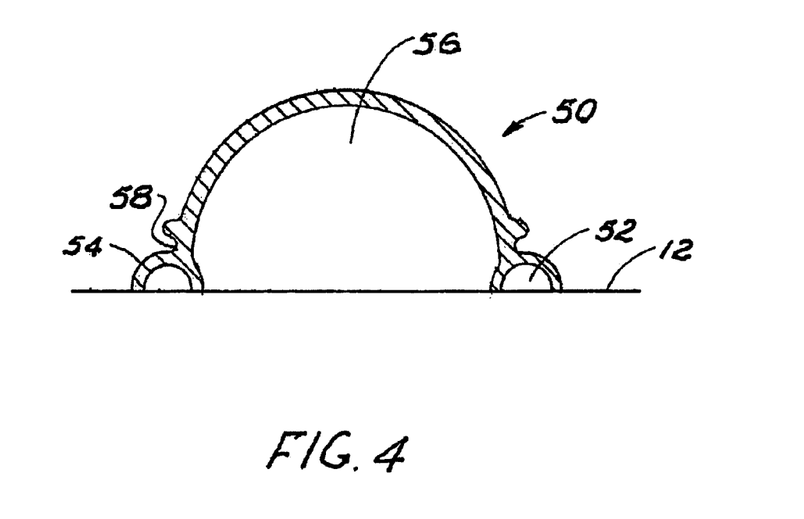
FIG. 4 is a section view of a dual chamber cup-shaped embodiment of the invention.

Enhanced bunching can also result from sequential application of vacuum is a dual chamber device. For example, as shown in FIG. 4, a cup shaped device 50 with a separate vacuum chamber 52 in its rim can be provided. Such a device can be semi-resilient or rigid in its construction. Suitable material is silicone rubber or polycarbonate, for example. In use, the rim 54 of the cup is placed against the patient's skin 12 and the rim chamber 52 evacuated, securing the cup to the skin. Next, the internal chamber 56 of the cup is evacuated, drawing the skin into conformance with the chamber 56, causing the tissue underlying the skin to bunch into the cup, increasing its thickness and drawing the resection cavity C toward the cup. Optionally, the cup shaped device 50 can be more resilient, and a groove 58 for a drawstring (not shown) can be provided to facilitate compaction of tissue under the device.

In an alternate method of use, the cup shaped device 50 could be positioned on the skin 12 and the central vacuum chamber 56 can be evacuated directly without first evacuating the rim chamber 52. Such use would facilitate tissue adjacent the device 50 to slide under the rim to more easily fill the chamber 56. This would be similar to use of a simple cup-shaped device (not shown) without a separate rim chamber for vacuum.

Figure 5A:
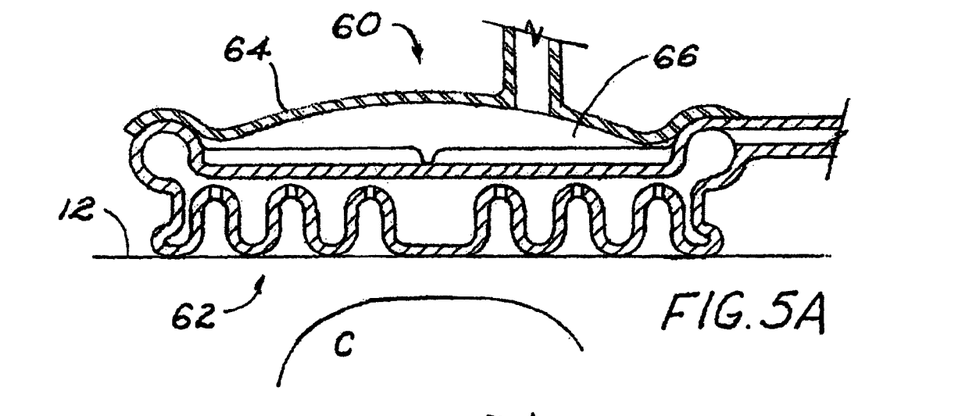
FIG. 5A is a section view of another dual chamber embodiment of the invention shown placed on the skin of the patient, overlying a resection cavity in the underlying tissue.
Figure 5B:
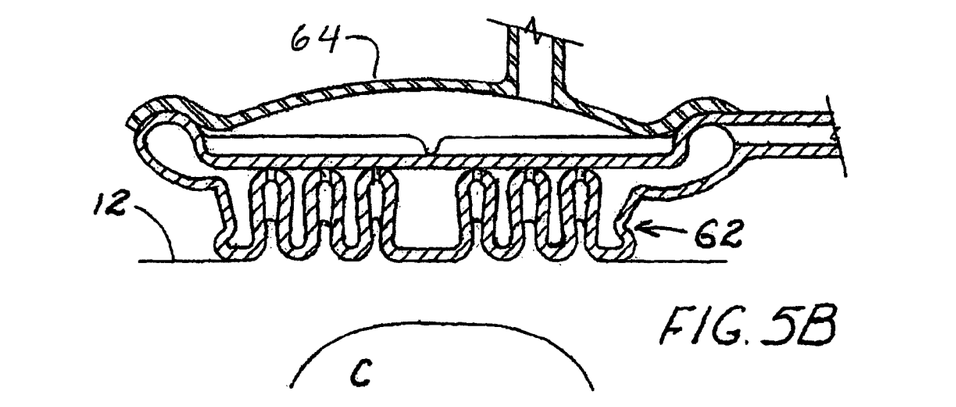
FIG. 5B is a section view of the device of FIG. 5A after fastening onto the skin by vacuum, showing a thickening of the tissue between the device and the resection cavity.
Figure 5C:
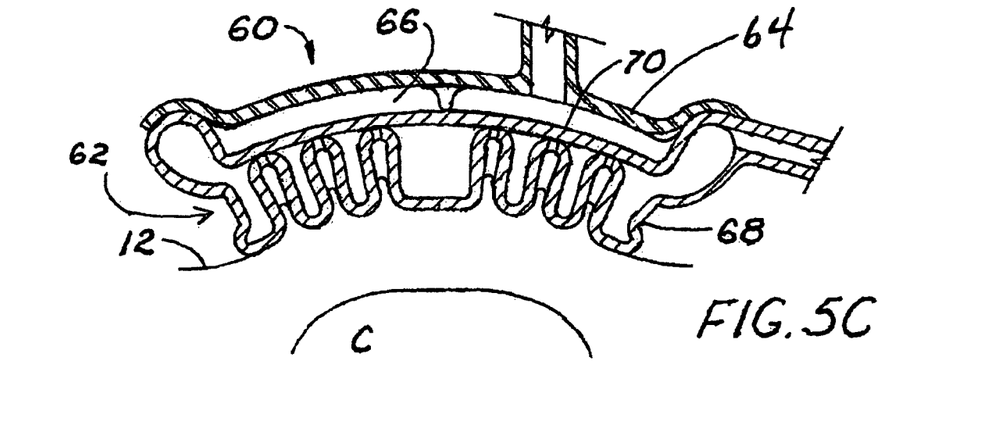
FIG. 5C is a section view of the device of FIGS. 5A and 5B after evacuation of a second chamber of the device, cupping the device and further thickening the tissue between the device and the resection cavity.

As shown in FIG. 5A, another dual-chambered embodiment 60 comprises a fully resilient element 62 shaped similarly to that of the device FIGS. 3A-D. In addition, a substantially rigid element 64 lies proximally of resilient element 62 and is secured thereto, for example by bonding or another conventional method. The rigid element 64 is shaped so as to create a secondary vacuum chamber 66 proximal of the resilient element 62, and to produce a desired contour at the skin surface once the resilient element 62 is secured to the skin 12 and the secondary chamber 66 is evacuated. FIG. 5B shows this embodiment with the resilient element 62 secured to the skin 12 and having contracted under vacuum, bunching the tissue over the resection cavity C. FIG. 5C shows the secondary vacuum chamber 66 evacuated and drawing the underlying tissue into configuration and further thickening the tissue between the device 60 and the resection cavity C. Optionally or as necessary, a drawstring (not shown) may be employed in a peripheral groove 68 of the resilient element to assist in tissue compaction under the resilient element 62. In a single-chambered variation of the device 60, the proximal resilient wall 70 of the device may be perforated (not shown), creating a single internal chamber.

Note also that a modified form of the device 60 can be preformed with a curved (partial spherical) contour at the skin-contacting distal end, i.e. with the undulating distal part 62 formed in a concave, curving or generally spherical shape, for application to the breast in this contoured form. Then vacuum can be applied to a single chamber.

In use, these devices are positioned over the treatment cavity and urged into contact with the skin. When the therapist is satisfied with placement, vacuum can be applied in a manner described above, providing temporary attachment to the skin by the suction force of the vacuum. If after attachment, the device's "footprint" has not spontaneously reduced due to the action of the vacuum on the device, it may be manually urged into a compacted state, or it may be diametrally compacted by cinching a peripheral belt or other appliance as described above in connection with the description of FIGS. 3A and 3B.

As mentioned above, other techniques can be used for moving the breast skin and underlying tissue so as to produce a deeper skin-to-cavity or skin-to-applicator distance (skin-to-balloon distance in the case of a balloon applicator used in the cavity). Adhesives can be used on skin-manipulating ends, provided the adhesive reliably grips the skin and is easily released (as by the means disclosed in the referenced U.S. Pat. No. 5,387,450), or by an appropriate solvent or simply by outward pulling force as opposed to the shear forces involved in the skin manipulation. The skin can be pushed along a selected pattern that does not amount to a closed circuit, and this can be essentially from one or more directions toward the region of inadequate tissue depth if desired. Simple friction can be used, via contacting lines or points that engage the skin, particularly the breast, so as to manipulate its pliable tissues to increase depth at a critical region. Manual methods of manipulation will also be appropriate in some situations, to urge the tissue in a desired direction where its position can then be maintained by any appropriate and reliable means to overcome a deficiency in skin-to-cavity depth at a particular location on the breast. Appropriate mechanical apparatus can include a clamp-like device with two jaws, either straight or concavely configured toward one another, and each with a high-friction (e.g. rubbery) contacting surface so as to bring tissue inward toward the critical region from opposed directions. The salient feature of this invention is that in a brachytherapy situation, when there is a region where the skin would be too close to the radiation source under the skin, the tissue (particularly in the case of a breast) is moved by some appropriate means, by engagement with the skin in such a way as to "bunch" the tissue under the skin adjacent to the treatment cavity at the critical region to meet minimum distance requirements from skin to cavity (actually, skin to inner radius of prescription dose region). This can include some form of ring (including a ring-shaped array) with adhesive or friction points or suction outlets to engage the exterior surface of the skin, with some provision for effectively reducing the diameter or size of the ring after skin engagement.

Confirmation of improved separation between treatment cavity and skin (thickness of tissue overlying the cavity) can be obtained by conventional imaging techniques (for example, x-ray or ultra-sound), if necessary with the help of a relatively radio-opaque, cavity-filling balloon within the cavity. Such reimaging will also assure no new thin regions have been created.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

I claim:

1. In a brachytherapy procedure performed using an applicator in a resection cavity of a living patient, a method for adjusting skin-to-cavity distance in a selected region to prevent over-radiation of the skin, comprising:
   engaging the skin from an area generally overlying or adjacent to the resection cavity and urging and moving the skin and intervening tissue between skin and cavity generally laterally toward the selected region from adjacent regions so as to gather the skin together to increase tissue depth between skin and cavity,
   performing a brachytherapy irradiation procedure treating tissue surrounding the resection cavity, using an applicator within the cavity, and
   maintaining increase in tissue depth during the brachytherapy irradiation procedure.

2. The method of claim 1, wherein the applicator is a balloon applicator.

3. The method of claim 1, wherein the resection cavity is the patient's breast.

4. The method of claim 1, wherein the step of engaging the skin, with pressure includes use of a ring with vacuum, channels and suction outlets engaged with the exterior surface of the skin, and the method including effectively reducing the diameter of the ring to draw additional tissue toward the selected region.

5. The method of claim 1, wherein the step of engaging the skin with pressure includes, use of vacuum channels and suction outlets engaging the exterior surface of the skin, and the method including effectively compacting the area of skin engagement to draw additional tissue toward the selected region.

6. The method of claim 1, wherein engaging the skin comprises engaging with vacuum and maintaining increase comprises maintaining a vacuum.

7. The method of claim 1, wherein engaging the skin comprises engaging with mechanical means.

8. The method of claim 1, wherein engaging the skin comprises engaging with adhesive or friction.

9. The method of claim 1, wherein the step of engaging the skin comprises using a vacuum-activated apparatus with multiple suction points to engage the skin around the selected region.

10. In a breast brachytherapy procedure wherein a balloon brachytherapy applicator is inserted into a resection cavity of the breast, a method for adjusting skin-to-balloon distance in a region to prevent over-radiation of the skin, comprising:
    determining a region where depth of tissue should be increased between the balloon and the skin surface, and
    engaging the breast externally with force so as to move breast tissue generally laterally to the determined region from surrounding regions, to increase the depth of tissue in the determined region to the extent that the skin-to-balloon distance is increased to prevent over-radiation, and maintaining the force during a brachytherapy irradiation treatment of breast tissue.

11. The method of claim 10, further including imaging to the breast just prior to commencing irradiation, to assure absence of remaining regions of inadequate distance.

12. The method of claim 10, wherein the step of engaging the breast with force includes engaging an array of temporary fastenings with the exterior surface of the breast and then contracting the temporary fastenings to draw breast tissue inwardly, pushing tissue toward the determined region.

13. The method of claim 10, wherein the step of engaging the breast with force comprises use of a cup over the breast, with a surface of the cup sealed against the skin of the breast, then placing a vacuum in an interior of the cup to draw the breast tissue to greater depth in the determined region.

14. The method of claim 10, wherein the step of engaging the breast with force comprises pushing the skin of the breast generally laterally from at least one side so as to bunch the breast tissue to greater depth at the determined region.

15. The method of claim 10, wherein the step of engaging the breast with force comprises engaging the skin of the breast at a plurality of points that define an array larger than the balloon, and drawing the skin inwardly relative to the array so as to bunch the breast tissue to greater depth at the determined region.

16. The method of claim 15, wherein the skin is engaged by friction at said points.

17. The method of claim 15, wherein the skin is engaged with adhesive at said points.

18. The method of claim 15, wherein the skin is engaged with suction at said points.

* * * * *